United States Patent
Russell et al.

(10) Patent No.: US 8,951,477 B2
(45) Date of Patent: *Feb. 10, 2015

(54) OZONE-BASED DISINFECTING DEVICE COMPRISING A FLOW SENSOR

(75) Inventors: Crispin Miles Russell, Cape Town (ZA); Mark Gregory Marshall, Cape Town (ZA); Clint Les Foster, Cape Town (ZA); Derek Hedley Rowles, Milnerton (ZA)

(73) Assignee: Arcaqua (Pty) Ltd., Cape Town (ZA)

(*) Notice: Subject to any disclaimer, the term of this patent is extended or adjusted under 35 U.S.C. 154(b) by 0 days.

This patent is subject to a terminal disclaimer.

(21) Appl. No.: 14/116,533

(22) PCT Filed: May 11, 2012

(86) PCT No.: PCT/IB2012/052355
§ 371 (c)(1),
(2), (4) Date: Nov. 8, 2013

(87) PCT Pub. No.: WO2012/153303
PCT Pub. Date: Nov. 15, 2012

(65) Prior Publication Data
US 2014/0154141 A1    Jun. 5, 2014

(30) Foreign Application Priority Data
May 12, 2011 (ZA) ................. 2011/03473

(51) Int. Cl.
| | |
|---|---|
| C02F 1/78 | (2006.01) |
| A23L 3/00 | (2006.01) |
| C02F 1/00 | (2006.01) |

(52) U.S. Cl.
CPC . *A23L 3/003* (2013.01); *C02F 1/78* (2013.01); *C02F 1/008* (2013.01); *C02F 2209/40* (2013.01); *C02F 2303/04* (2013.01); *C02F 2307/06* (2013.01)

USPC .............................. 422/119; 422/19

(58) Field of Classification Search
CPC .... A61L 2/202; C02F 1/4672; C02F 2201/78
USPC ............................. 422/119, 28, 29
See application file for complete search history.

(56) References Cited

U.S. PATENT DOCUMENTS

| | | | |
|---|---|---|---|
| 4,462,264 A * | 7/1984 | Feller | ............ 73/861.18 |
| 7,875,173 B1 | 1/2011 | Barnes | |

FOREIGN PATENT DOCUMENTS

WO    2010/001279 A1    1/2010

OTHER PUBLICATIONS

WIPO, International Search Report and Written Opinion for PCT/IB2012/052355, Nov. 5, 2012.

*Primary Examiner* — Sean E Conley
*Assistant Examiner* — Donald Spamer
(74) *Attorney, Agent, or Firm* — Remenick PLLC

(57) ABSTRACT

An ozone-based disinfecting device is provided comprising a mixer having a generally hollow body with a water inlet for water under pressure, a spray nozzle for generating a generally conical spray of water introduced by way of the water inlet, a contact chamber communicating with a gas inlet for ozone rich gases, and an outlet aperture from the contact chamber that is coaxial with the spray nozzle and spaced apart therefrom. An electronic flow sensing device senses the extent of the flow of water through the spray nozzle according to vibration caused by water flowing through the mixer. The electronic flow sensing device is preferably located in a pocket formed in the mixer and preferably comprises a piezoelectric sensor embedded at least around its periphery in a settable material. A preferred construction of the mixer is also described.

12 Claims, 5 Drawing Sheets

OZONE-BASED DISINFECTING DEVICE COMPRISING A FLOW SENSOR

REFERENCE TO RELATED APPLICATIONS

This application is a National Stage filing and claims priority to International Application No. PCT/IB2012/52355 of the same title filed May 12, 2012, and also claims priority to South African Application No. 2011/03473 filed May 12, 2011.

FIELD OF THE INVENTION

This invention relates to an ozone-based disinfecting device of the general nature in which the device, in use, generates a water spray having an effective and appropriate quantity of ozone embodied therein. More particularly, the invention relates to an ozone-based disinfecting device that is suitable for use in relation to food, although it may be used in many other applications.

Still more particularly, the invention relates to a disinfecting device of the general nature described in our earlier published international patent application WO 2010/001279.

BACKGROUND TO THE INVENTION

Microbial outgrowth is a primary concern in the food processing industry and amongst consumers. The presence of pathogenic microorganisms on food products can potentially lead to food-borne outbreaks of disease.

Chlorine-based chemicals such as sodium hypochlorite, calcium hypochlorite, sodium dichloroisocyanurate and quaternary ammonium compounds have been employed for disinfecting food products in the past. However, chlorine is most effective at a pH of 6 to 8, and becomes less effective outside of this pH range. Also, chlorine can produce toxic byproducts that are harmful to human health, such as chloramines and trihalomethanes.

As a result of this, the European Union has imposed a bar against the use of chlorine compounds for disinfecting food produce, as specified by the EU Directive 2092/91. There has consequently been a concerted effort to improve technology employing non-chlorine based products for the treatment of food products to disinfect them. This has resulted in an increased interest in the disinfecting properties of ozone. The use of ozone for disinfecting food has been approved by the United States Food and Drug Administration (FDA).

It is noted that ozone is reported to have about 1.5 times the oxidizing potential of chlorine with contact times for the anti-microbial action of ozone being typically four to five times less than that of chlorine.

Ozone has been shown to be a highly reactive oxidant that is capable of killing microorganisms such as bacteria as well as reacting with other chemicals such as pesticides and herbicides. Of course, a major advantage of ozone is its natural decomposition into oxygen and thus its use in disinfecting food products is highly beneficial as it decomposes into a non-toxic gas. It therefore does not impart odour to, or taint, food products and no residual compounds or toxic residue remain. Rinse water can be discharged to the environment or used for other applications without additional treatment or decontamination.

In prior art disinfecting processes known to applicant to use ozone, venturi injection systems and bubble diffusers have been used to mix ozone into water. In the case of venturi injectors, water is forced through a convergent conical body, initiating a pressure differential between the inlet and the outlet of the system. This creates a vacuum inside the body of the injector, thereby initiating a flow of ozone rich air through a suction port.

As regards bubble diffusers, ozone rich air is emitted in bubbles beneath the surface of the water. Irrespective of the problems further identified below, bubble diffusers suffer from an inherent disadvantage in that diffuser holes frequently become fouled over time thereby decreasing the efficiency of the system.

In both instances, ozone is dissolved into the water, typically from an ozone rich air, and an appreciable proportion of the sterilizing ability of the ozone may be spent in sterilizing the water itself. This leaves a reduced amount of ozone available for effective disinfecting of the ultimate target that may be fresh produce, for example.

Furthermore, these prior art systems appear to allow free gaseous ozone to be released into the atmosphere in higher concentrations than is permitted by regulatory standards. It is to be noted that free ozone in the air is harmful when it exceeds predetermined concentrations.

In this regard it is to be noted that in the European Union, the current target value for ozone concentrations is reported to be 120 µg/m$^3$ which is about 60 nmol/mol. This target applies to all member states in accordance with Directive 2008/50/EC although there is no date set for formalizing this as a requirement and it is treated as a long-term objective. In the USA, in May 2008, the Environmental Protection Agency (EPA) lowered its ozone standard from 80 nmol/mol to 75 nmol/mol. This was done in spite of the fact that the Agency's own scientists and advisory board had recommended lowering the standard to 60 nmol/mol. The EPA has developed an Air Quality Index to help explain air pollution levels to the general public and presently the current standards describe an eight-hour average ozone mole fraction of 85 to 104 nmol/mol as "unhealthy for sensitive groups"; 105 nmol/mol to 124 nmol/mol as "unhealthy"; and 125 nmol/mol to 404 nmol/mol as "very unhealthy". The World Health Organization recommends 51 nmol/mol.

Excess ozone in the air is therefore quite undesirable and it is important that any disinfecting device using ozone as its active disinfecting medium should not release any appreciable quantities of ozone into the atmosphere, whilst providing an effective concentration to destroy target bacteria etc.

In our earlier international patent application identified above, the proposal for sensing water flow through a mixer was to monitor the increase in pressure in the mixer when water was applied under pressure to the mixer. This expedient did not operate effectively and alternative controls needed to be investigated.

SUMMARY OF THE INVENTION

In accordance with this invention there is provided an ozone-based disinfecting device comprising a mixer having a generally hollow body with a water inlet for water under pressure; a spray nozzle for generating a generally conical spray of water introduced by way of the water inlet; a contact chamber communicating with a gas inlet for ozone rich gases; an outlet aperture from the contact chamber with the outlet aperture being coaxial with the spray nozzle and spaced apart therefrom, and a flow sensing device for sensing the extent of flow of water through the spray nozzle, the ozone-based disinfecting device being characterized in that the flow sensing device is an electronic flow sensing device for sensing vibration caused by a flow of water through the mixer.

Further features of the invention provide for the electronic flow sensing device to be located in a pocket provided in the mixer body; for the electronic flow sensing device to include a piezoelectric sensor and an appropriate associated circuit for generating a signal indicative of the rate of flow of water through the mixer; and for the piezoelectric sensor to be embedded in a settable material and have the general shape of a disc that has a thin smaller diameter compressible disc adhered concentrically to both surfaces of the sensor disc with the outer diameter of the piezoelectric sensor firmly embedded in the settable material and wherein a small hole in the centre of one disc provides for the settable material to contact the piezoelectric sensor in the central region on the one side thereof.

Still further features of the invention provide for an associated circuit to be carried on a printed circuit board housed within the mixer body; for the printed circuit board to be housed in a pocket in the mixer body; for the flow sensing device and an associated circuit to be arranged to activate and deactivate an ozone generator operatively connected to the gas inlet for ozone rich gases; for a signal outputted by the flow sensing device and associated circuit to operatively activate and deactivate a fan supplying air to the ozone generator with activation of the fan being effected before activation of the ozone generator takes place and deactivation of the fan being effected after deactivation of the ozone generator takes place; and for the fan to be capable of running at different speeds dependent on the flow rate of water through the spray nozzle.

Additional features of the invention provide for the diameter of the outlet aperture to correspond substantially to the diameter of the conical spray at that position so that substantially no free space exists between the outside of the conical spray and the periphery of the outlet, in use; for the contact chamber itself to have a larger cross-sectional size than the diameter of the outlet aperture; and for the gas inlet for ozone rich gases to have an axis parallel to, but laterally offset from, that of the water inlet with a gas inlet chamber merging laterally with the contact chamber.

The mixer body is preferably composed of a first part in the form of a shroud defining the outlet aperture that receives, in an open end opposite the outlet aperture, a second part defining the water inlet, gas inlet and a pocket for receiving the electronic flow sensing device for sensing the extent of flow of water through the spray nozzle with the second part of the body being received in the open end of the shroud part of the body in plug-like manner.

The water inlet is preferably configured as a screw threaded socket for application directly to a complementarily screw threaded spout of a tap or other tubular water dispensing item.

In accordance with a second aspect of the invention there is provided an ozone-based disinfecting device comprising a mixer as defined above; an ozone generator operatively connected to the gas inlet for ozone rich gases in the mixer; and a control circuit connected to the flow sensing device and any associated circuit, wherein the control circuit is configured to activate the ozone generator once a signal is received from the flow sensing device and any associated circuit corresponding to a minimum flow rate of water through the mixer that is required to develop a suitable spray cone of water occupying the outlet aperture from the contact chamber and to deactivate the ozone generator once the signal received corresponds to less than said minimum flow rate.

It is to be noted that practice of the present invention results in ozone rich gases becoming entrained with multitudinous water droplets of the spray and it is believed that the ozone adheres itself in some way, possibly electromagnetically or electro-statically, to the surface of the water droplets without any appreciable proportion of the ozone becoming dissolved in the water. This theory explains the practical measurements taken to date that indicate that more ozone is carried by the water than would normally be soluble in it. Tests conducted to date have also revealed that there is substantially no free ozone in the air surrounding the disinfecting spray and there is little or no ozone remaining in the spent water. Practice of the invention apparently approaches optimal use of ozone and enables it to be highly effective in its disinfecting activity.

Whilst the mechanism of the attachment or otherwise of ozone molecules to the water droplets of the spray is not yet fully understood, or fully researched technically, tests conducted to date indicate that the droplet size developed by the spray is preferably between 10 and 50 μm and the water spray cone preferably has a cone angle of between 35° and 45°. Also, the flow developed by the fan and the reduction in pressure created by the flow of the conical spray out of the outlet aperture, is such that a slightly negative pressure, of the order of 10 mm of water (100 Pa), is maintained within the contact chamber. In this regard, further tests will be directed at establishing whether or not it is practical to do away with the fan completely and this will depend largely on the negative pressure that is generated within the contact chamber and the nature of the flow path through the ozone generator to the mixer.

In order that the above and other features of the invention may become more apparent, one embodiment embracing all of the different aspects of the invention will now be described with reference to the accompanying drawings.

DETAILED DESCRIPTION WITH REFERENCE TO THE DRAWINGS

Figure 1:
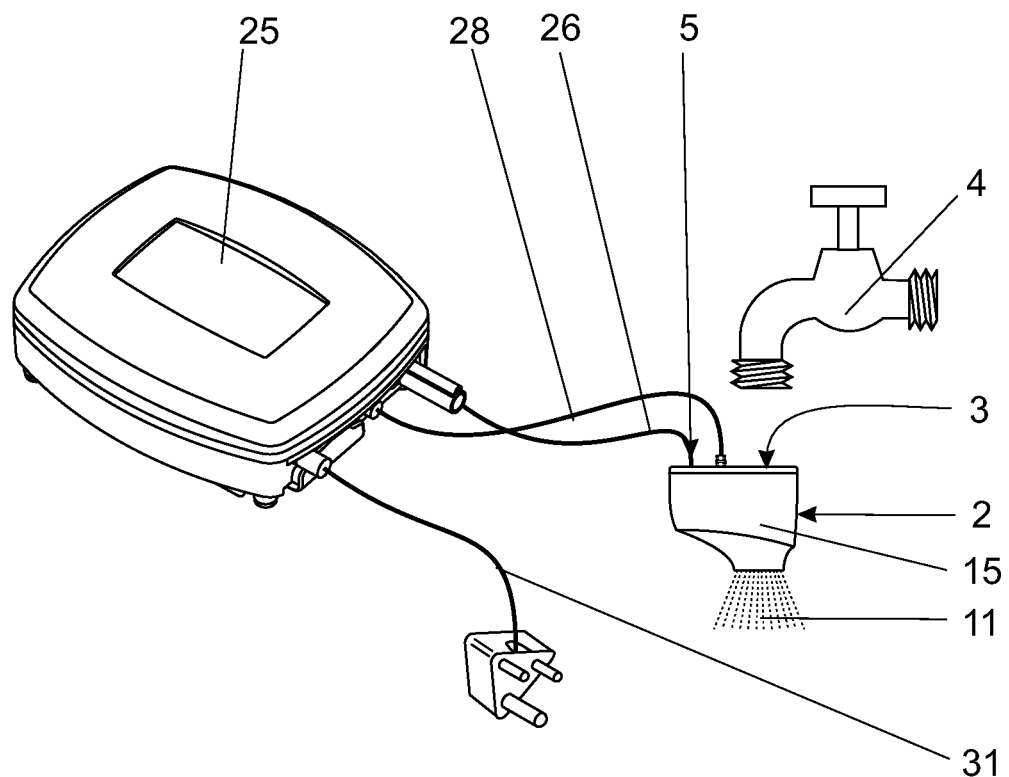
FIG. 1 is a schematic illustration of the various components of an ozone-based disinfecting device according to the invention.
Figure 2:
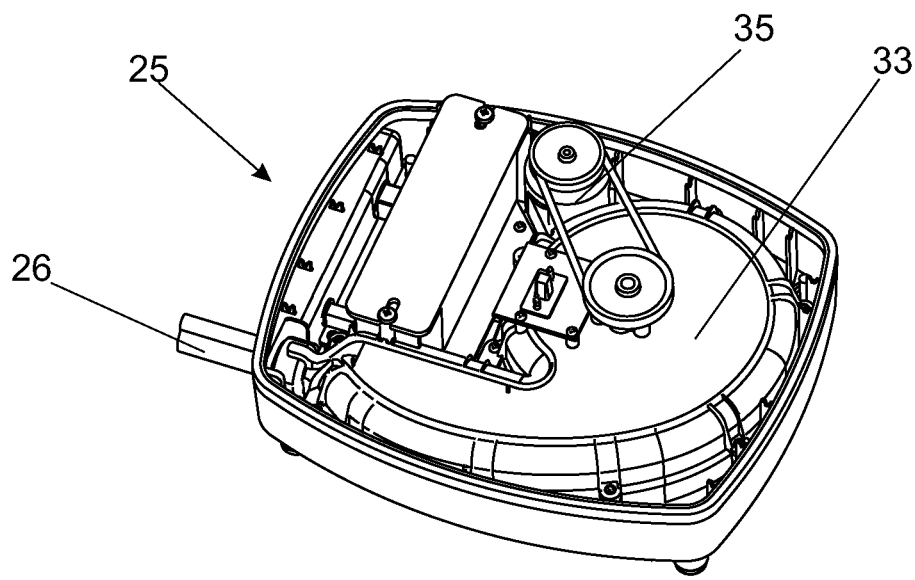
FIG. 2 is an illustration of the ozone generator used in the device illustrated in FIG. 1 with its cover removed.

In the embodiment of the invention illustrated in the drawings, an ozone-based disinfecting device comprises a mixer (2) having a generally hollow body with a screw threaded socket (3) as a water inlet for water under pressure with the socket being adapted for direct connection to a screw threaded outlet from a water supply tap (4) or some other water supply device having a tubular outlet.

A gas inlet (5) for ozone rich gases has its axis parallel to, but laterally offset from, that of the water inlet with a gas inlet chamber (6) merging laterally with an otherwise generally cylindrical contact chamber (7) surrounding the water inlet. The mixer has a spray nozzle (8) that embodies a swirler (9) (see FIG. 4) for generating a generally conical spray (11) of water introduced by way of the water inlet (see FIG. 5) such that a conical spray is directed into the contact chamber and towards a coaxial reduced diameter outlet aperture (12) spaced apart therefrom. The contact chamber itself has a larger cross-sectional size than the diameter of the outlet aperture. The spray nozzle is coaxial with the water inlet and the nozzle itself is located generally centrally in the contact chamber.

The diameter of the outlet aperture corresponds substantially to the outer diameter of the conical spray at that distance from the nozzle so that substantially no free space exists between the outside of the conical spray and the periphery of the outlet. In fact, in use, the outer perimeter of the conical spray may be cut off slightly by the periphery of the outlet aperture although care should be taken that the extent of this should not cause larger droplets to coalesce on the perimeter of the outlet.

As regards the construction of the mixer body, it is conveniently composed of a first part (15) in the form of a shroud defining the outlet aperture and an open end opposite the outlet aperture that receives a second part (16) defining the water inlet, gas inlet, as well as a pocket (17) between the water inlet and gas inlet. The lateral merging of the gas inlet chamber and contact chamber, in this instance, takes place on the sides and beneath the pocket.

Figure 4:
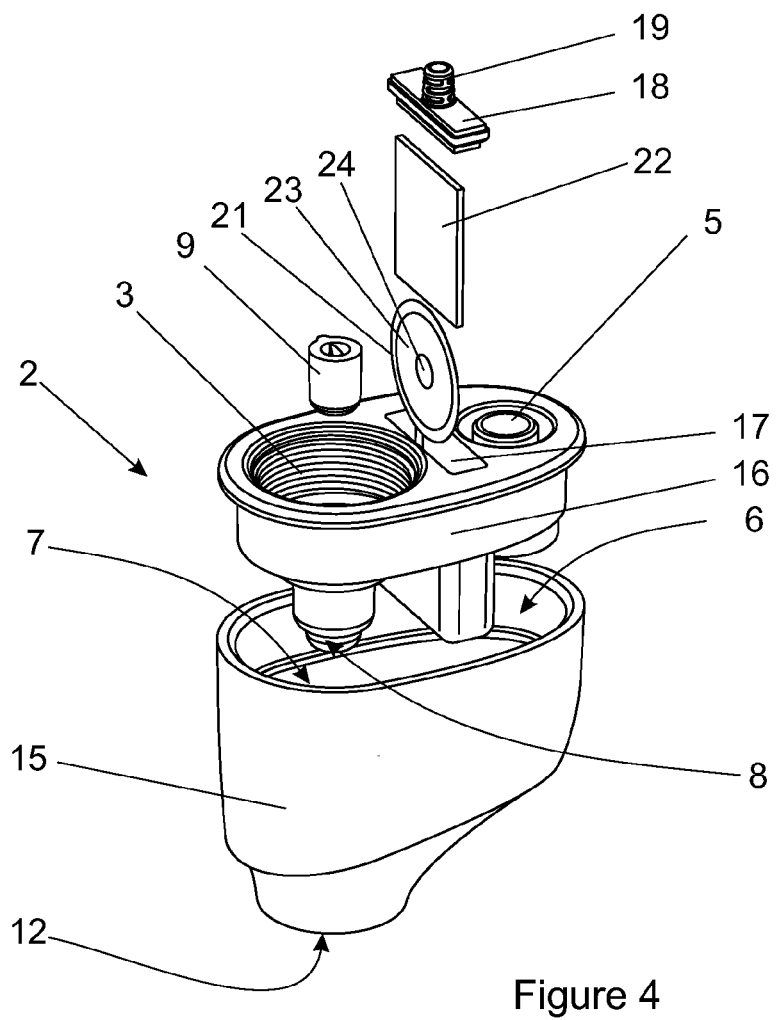
FIG. 4 is an exploded perspective view of the mixer illustrated in FIG. 1.
Figure 5:
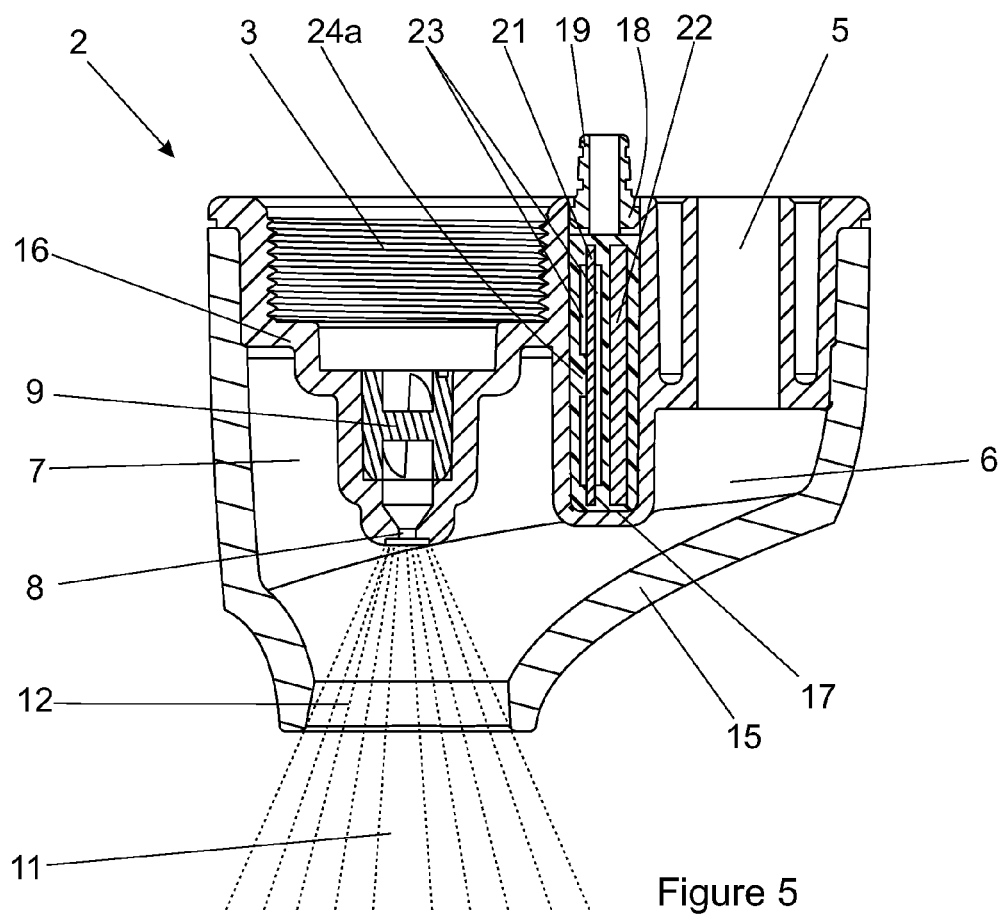
FIG. 5 is a sectional elevation of the mixer illustrated in FIGS. 1 and 4.
Figure 6:
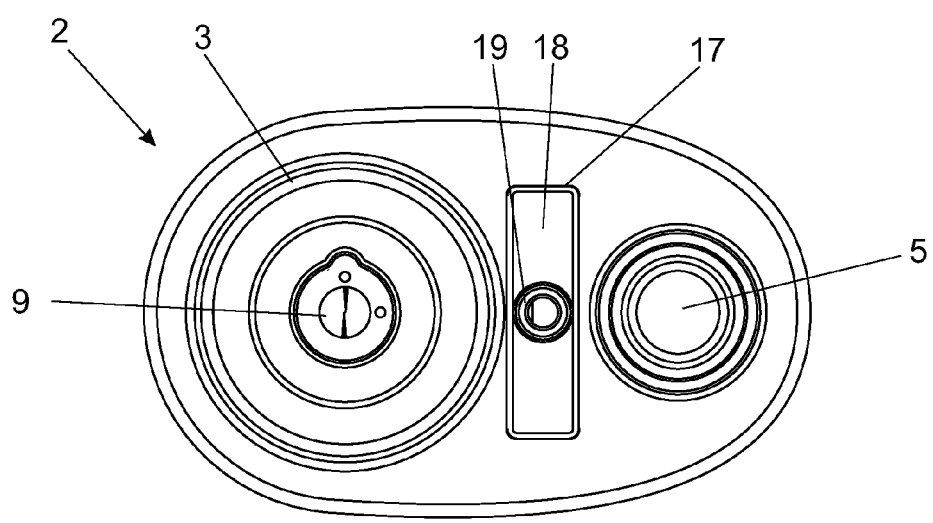
FIG. 6 is a plan view of the mixer.

The second part of the body is received in the open end of the shroud part of the body in plug-like manner, as will be most apparent from FIG. 4 of the accompanying drawings. Both the first and second parts of the mixer body may be injection moulded or die cast from suitable ozone resistant material and the two parts may be permanently sealed together in any suitable manner including ultrasonic welding, solvent welding and adhesive. The opening to the pocket may be closed by a suitable closure (18) that may have its own flexible cord collar (19) as shown in FIG. 4.

The mixer includes a flow sensing device in the form of a piezoelectric sensor (21) that is connected to an associated circuit in the form of an electronic signal generating printed circuit board (22) that serves to amplify signals generated by the piezoelectric sensor and provide an output appropriate for operating a control circuit that is described further below.

In order to ensure that the piezoelectric sensor is activated adequately by the vibration created by water passing through the mixer, the piezoelectric sensor itself, as well as its associated circuit in the form of the printed circuit board (22), are received in the pocket (17) in the mixer body and the remaining space within the pocket is filled with a suitable settable material. The settable material will thus ensure that vibrations generated are properly transferred to the piezoelectric sensor.

In one successful arrangement of the piezoelectric sensor it has the shape of a disc with a thin smaller diameter compressible, in this instance foam, disc (23) adhered concentrically to both surfaces of the sensor. The smaller outer diameter of the foam discs enables the outer periphery of the piezoelectric sensor to become firmly embedded in the settable material. A small hole (24) (see FIG. 4) in the centre of the foam disc that is closer to the socket allows the settable material to contact the piezoelectric sensor in the central region on the one side thereof. The effect is that the piezoelectric sensor, being firmly held around its periphery and excited by the small pillar (indicated by numeral (24a) in FIG. 5) of settable material occupying the small hole (24), exhibits enhanced movement as a result of the fact that the foam allows the enhanced vibration of the piezoelectric sensor with a correspondingly enhanced output therefrom.

Figure 8:
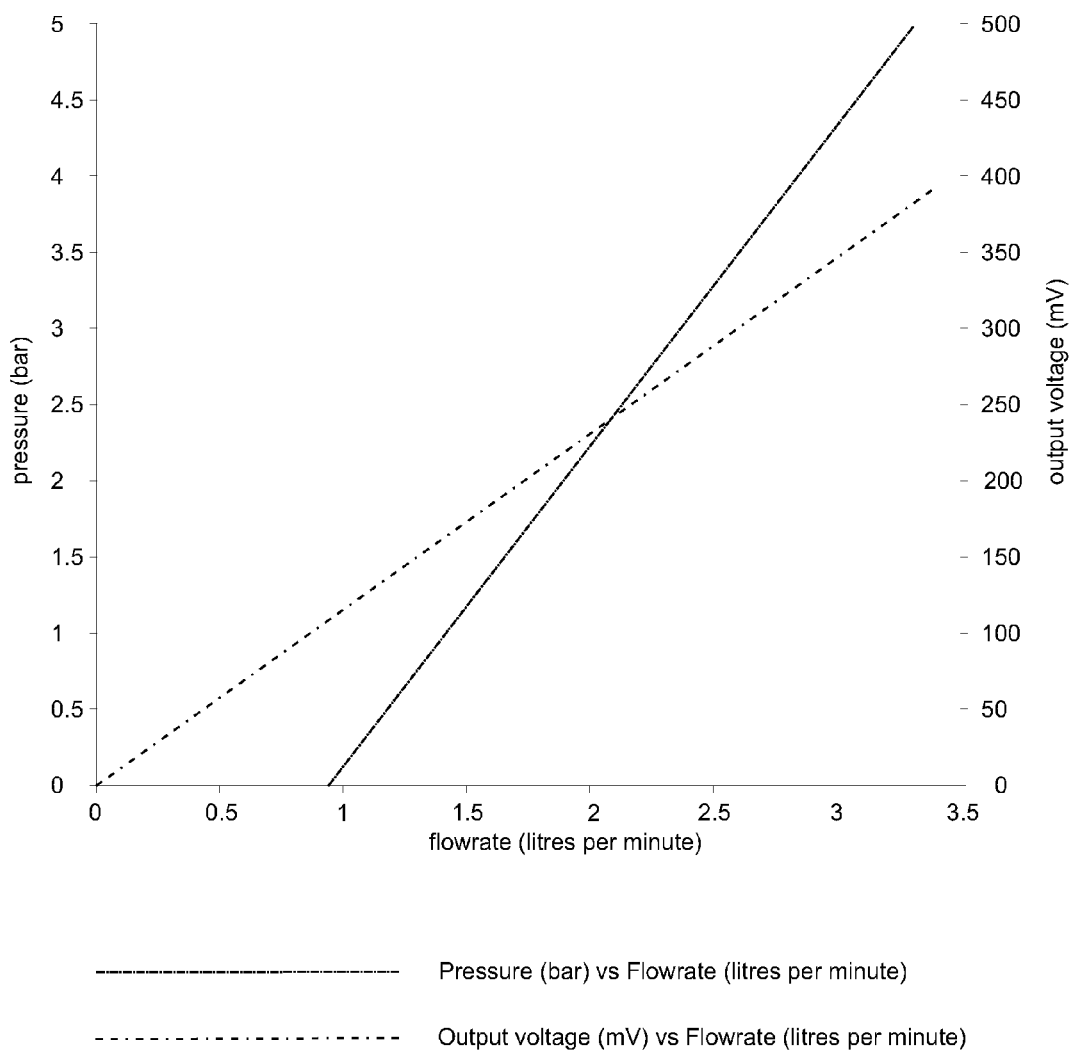

Of course, the piezoelectric sensor is sensitive to vibration set up by water as it passes through the nozzle and the vibration will vary, typically in frequency, with the flow rate of water. FIG. 8 is a graph illustrating the variation of flow rate with pressure and the output from the piezoelectric sensor and associated circuit.

A microprocessor (41) is preferably included on the printed circuit board and this enables other intelligent electronic sensors to be incorporated in the mixer circuit such as an infrared proximity sensor (42) for switching on the nozzle as well as for connection to a solenoid controlled water valve in which instance it can switch on the water flow itself. The sensor could thus be used for switching on ozonated flushing water in a urinal, for example.

Figure 7:
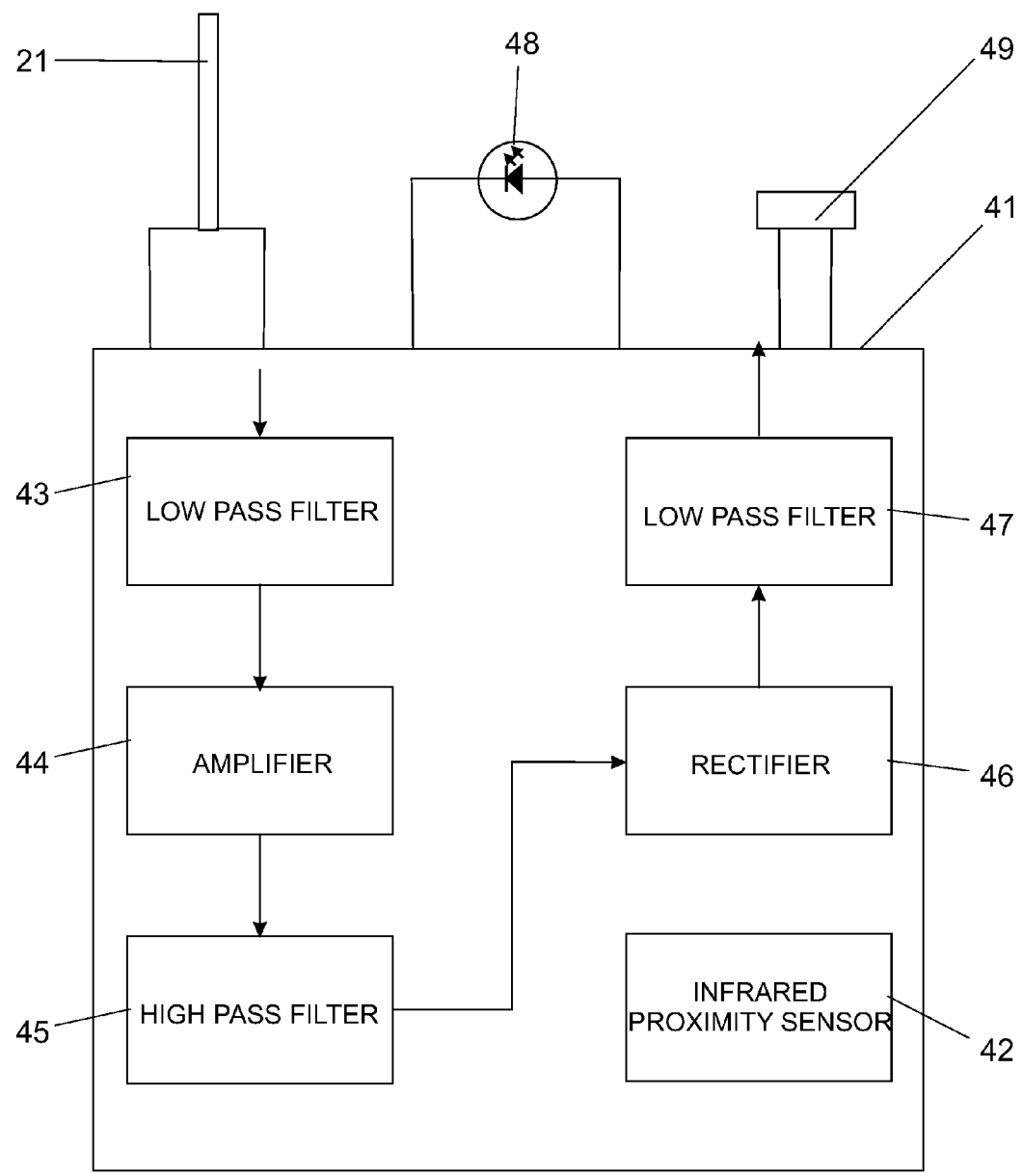
FIG. 7 is a block circuit diagram of the circuit of the piezoelectric detection circuit; and, FIG. 8 is a graph showing the variation of output from the piezoelectric sensor and associated circuit and to the water pressure as against flow rate through the mixer.

Simply for the sake of completeness, an example of an electronic circuit is illustrated in block diagram form in FIG. 7. It will be noted that the output from the piezoelectric sensor is firstly passed through a low pass filter (43) and subsequently through an amplifier (44). The amplified signal is passed through a high pass filter (45) followed by a rectifier (46) and thereafter a low pass filter (47). Of course the electronic circuit can include a light emitting diode (LED) (48) to indicate when the vibration sensor is excited. Also an additional function of the LED in the mixer, or an additional LED, could be to communicate other information to a user such as to show timing intervals by flashing every 15 seconds thereby aiding in dosing washed items correctly. It can also show errors or unit faults by flashing sequences of red (as opposed to green or blue) light. The printed circuit board may be provided with a communications connector (49) for connection to the ozone generator is further described in what follows.

Figure 3:
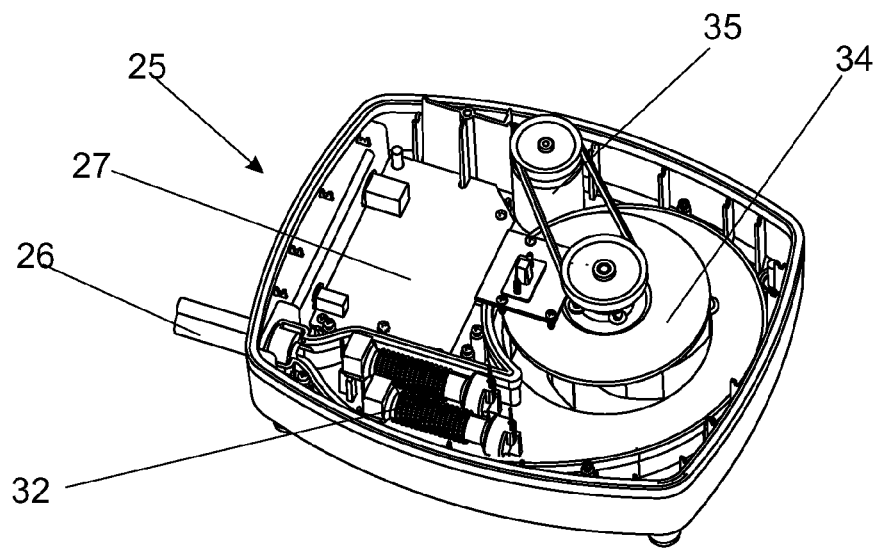
FIG. 3 is a similar illustration of the ozone generator with certain components removed in order to reveal others.

A separate ozone generator (25) of generally known construction and of the corona discharge type is operatively connected by way of a suitable tube (26) to the gas inlet (5) for ozone rich gases to the mixer. The ozone generator is, however, modified to operate in terms of this invention and houses a control circuit on a printed circuit board (27) (see FIG. 3) within the ozone generator housing.

The ozone generator is also connected to the mixer by way of a communications cable (28) that serves to supply the printed circuit board (22) and piezoelectric sensor (21) in the pocket within the mixer with electrical energy at a low DC voltage and to convey signals generated in response to the piezoelectric sensor to the control circuit in the ozone generator housing.

The control circuit incorporates a suitable transformer and rectifier for connection by way of a suitable cable (31) to an electrical mains power outlet supply. The control circuit is configured to activate a corona discharge ozone generator unit (32) once a signal is received from the mixer corresponding to a minimum predetermined flowrate of water through the mixer that will correspond to the development of a spray cone of water occupying the outlet aperture from the contact chamber. The control circuit similarly deactivates the ozone generator unit once the signal received from the mixer corresponds to less than said minimum flow rate. It will be understood that, in this manner, the generation of ozone in the absence of an adequate flow of water through the mixer is avoided and ozone cannot be liberated into the atmosphere in consequence.

The ozone generator, in this embodiment of the invention, also includes a variable speed centrifugal fan (33) for blowing air through the ozone generator and thence into the contact chamber of the mixer. The centrifugal fan has a substantially conventional centrifugal impeller (34) that is driven by a variable speed DC electric motor (35). The variable speed electric motor is controlled by the control circuit in response to signals received from the piezoelectric sensor such that the fan is activated before activation of the ozone generator takes place and is deactivated after deactivation of the ozone generator takes place.

In use a disinfecting spray of water carrying ozone as an active disinfectant is generated with the spray passing through the contact chamber and out of the outlet aperture so that ozone is carried with the spray out of the outlet, as described above.

Operation of the disinfecting device is initiated by opening the tap to cause water to flow through the mixer and once the flowrate reaches a minimum level of, in this instance about 1.3 liters per minute, and preferably between 1.6 and 2 liters per minute, the control circuit will firstly switch on the DC motor that drives the fan to establish an airflow over the corona discharge unit (32) and, shortly afterwards, the high-voltage circuit of the corona discharge unit is energized to start generating ozone. This routine is followed to make sure that all of the ozone that is generated is carried through to the mixer. The control circuit may also switch on an indicator light such as a blue LED to indicate that the air is flowing and that ozone is being generated.

As the tap is opened further the piezoelectric sensor in the nozzle causes a signal of increased flow to be sent to the control circuit which adjusts the fan speed to increase the airflow in response to the increased water flow. The disinfecting device thus has the ability to sense the rate of water flow and to supply an increased amount of ozone to the mixer when the water flowrate increases.

The mixed ozone and water leave the nozzle in fine droplet/spray form and hit the target which is placed or handled in the water spray where it is cleaned.

Thus the air is blown by the fan through the corona discharge unit at a speed that is variable according to the signal received from the piezoelectric sensor and its associated circuit. In this regard, it is to be noted that the piezoelectric sensor senses vibration created by the passage of water through the swirler and nozzle of the mixer and the properties of the vibrations will vary with the flowrate of water through the mixer.

Simply by way of example, in test equipment employed, the following pressures resulted in the stated flow rates of water and fan speeds with the stated ozone content of the water:—

| Pressure Bar | Flow Rate litres/min | Fan Speed RPM | Ozone Content ppm |
| --- | --- | --- | --- |
| 2 | 1.3 | 2000 | 26 |
|  |  | 2500 | 29 |
|  |  | 3000 | 29 |
| 2.5 | 1.5 | 2000 | 26 |
|  |  | 2500 | 28 |
|  |  | 3000 | 28 |
| 3 | 1.7 | 2000 | 22 |
|  |  | 2500 | 25 |
|  |  | 3000 | 25 |
| 3.5 | 1.8 | 2000 | 22 |
|  |  | 2500 | 25 |
|  |  | 3000 | 25 |
| 4 | 1.9 | 2000 | 22 |
|  |  | 2500 | 23 |
|  |  | 3000 | 24 |

In spite of the foregoing, it is to be noted that it is also envisaged that the slightly reduced pressure created in the mixing chamber by virtue of the spray moving through it, may be enough to induce a satisfactory flow of air through the ozone generator thereby rendering the fan and its associated controls not necessary with a consequent saving in cost. However, in such an instance, the pressure of the water supply should be relatively consistent within a predetermined practical range available from water mains.

Numerous variations and applications exist for the invention. Thus, for example, a portable unit could be produced as a self contained shoulder slung unit with a water reservoir, a battery pack and an atomizing lance. A user could walk around an area sanitizing equipment for gyms or other large areas that cannot tolerate large volumes of water.

The nozzle could be attached to a dishwasher in order to supply a constant sanitizing spray during a wash cycle. This arrangement may allow a dishwasher to have its operating temperature reduced so as to save electricity.

The nozzle could be attached to an overhead misting type of system to create a gentle cooling mist over fresh produce to cool and sanitize in many situations such as a market, a transport vehicle, or any other appropriate environment.

The device could be used in a tunnel with a conveyor and multiple nozzles could be spaced apart along the length of the tunnel for large volume items that need to be sanitized. Such an arrangement could be used to sanitize fish packing crates or any other fresh produce packing crates. This system could also be used to sanitize and remove pesticides on high volumes of fresh produce in packing houses.

The disinfecting device could be connected to a urinal so as to spray ozone enriched water into the urinal upon flushing. In this way bacteria and odours could be reduced.

The unit may be an under-counter or wall mounted unit associated with a dedicated wash basin, for example.

Numerous variations of the invention exist without departing from the scope hereof.

The invention claimed is:

1. An ozone-based disinfecting device comprising a mixer having a generally hollow body with a water inlet for water under pressure; a spray nozzle for generating a generally conical spray of water introduced by way of the water inlet; a contact chamber communicating with a gas inlet for ozone rich gases; an outlet aperture from the contact chamber with the outlet aperture being coaxial with the spray nozzle and spaced apart therefrom, and a flow sensing device for sensing the extent of flow of water through the spray nozzle, wherein the flow sensing device is an electronic flow sensing device for sensing vibration caused by a flow of water through the mixer and comprises a piezoelectric sensor and an appropriate associated circuit for generating a signal indicative of the rate of flow of water through the mixer, wherein the piezoelectric sensor is embedded in a settable material and has the general shape of a disc that has a thin smaller diameter compressible disc adhered concentrically to both surfaces of the sensor disc with the outer diameter of the piezoelectric sensor firmly embedded in the settable material and wherein a small hole in the center of one disc provides for the settable material to contact the piezoelectric sensor in the central region on the one side thereof.

2. An ozone-based disinfecting device as claimed in claim 1 in which the electronic flow sensing device is located in a pocket provided in the mixer body.

3. An ozone-based disinfecting device as claimed in claim 1 in which the associated circuit is carried on a printed circuit board housed within the mixer body.

4. An ozone-based disinfecting device as claimed in claim 3 in which the printed circuit board is housed in a pocket in the mixer body.

5. An ozone-based disinfecting device as claimed in claim 1 in which the flow sensing device and an associated circuit is arranged to activate and deactivate an ozone generator operatively connected to the gas inlet for ozone rich gases.

6. An ozone-based disinfecting device as claimed in claim 1 in which a signal outputted by the flow sensing device and associated circuit operatively activates and deactivates a fan supplying air to the ozone generator with activation of the fan being effected before activation of the ozone generator takes place and deactivation of the fan being effected after deactivation of the ozone generator takes place.

7. An ozone-based disinfecting device as claimed in claim 6 in which the fan is capable of running at different speeds dependent on the flow rate of water through the spray nozzle.

8. An ozone-based disinfecting device as claimed in claim 1 in which the diameter of the outlet aperture corresponds substantially to the diameter of the conical spray at that position so that substantially no free space exists between the outside of the conical spray and the periphery of the outlet, in use.

9. An ozone-based disinfecting device as claimed in claim 1 in which the contact chamber itself has a larger cross-sectional size than the diameter of the outlet aperture.

10. An ozone-based disinfecting device as claimed in claim 1 in which the gas inlet for ozone rich gases has an axis parallel to, but laterally offset from, that of the water inlet with a gas inlet chamber merging laterally with the contact chamber.

11. An ozone-based disinfecting device as claimed in claim 1 in which the mixer body is composed of a first part in the form of a shroud defining the outlet aperture that receives, in an open end opposite the outlet aperture, a second part defining the water inlet, gas inlet and a pocket for receiving the electronic flow sensing device for sensing the extent of flow of water through the spray nozzle with the second part of the body being received in the open end of the shroud part of the body.

12. An ozone-based disinfecting device as claimed in claim 1 in which the water inlet is configured as a screw threaded socket for application directly to a complementarily screw threaded spout of a tap or other tubular water dispensing item.

* * * * *